United States Patent [19]

Törnblom

[11] Patent Number: 4,734,642

[45] Date of Patent: Mar. 29, 1988

[54] DEVICE FOR USE IN EDDY CURRENT TESTING FOR TRANSMISSION OF SIGNALS BETWEEN A SIGNAL PROCESSING DEVICE AND A SIGNAL SOURCE

[75] Inventor: Bengt H. Törnblom, Västerås, Sweden

[73] Assignee: Tornbloms Kvalitetskontroll AB, Sweden

[21] Appl. No.: 816,270

[22] Filed: Jan. 6, 1986

[30] Foreign Application Priority Data

Jan. 8, 1985 [SE] Sweden .............................. 8500065

[51] Int. Cl.⁴ .................. G01N 27/90; H01R 35/00
[52] U.S. Cl. ........................................ 324/226; 74/660;
174/86; 324/238; 324/262; 439/8; 439/13
[58] Field of Search .............................. 324/219–221,
324/226, 234–240, 262; 174/86; 74/319, 660;
439/6, 8, 13, 164

[56] References Cited

U.S. PATENT DOCUMENTS

| 2,666,188 | 1/1954 | Klein ................................. 174/86 X |
| 3,109,139 | 10/1963 | Branker ............................... 324/240 |
| 4,409,549 | 10/1983 | Garner et al. ........................ 324/262 |
| 4,441,078 | 4/1984 | Lecomte .......................... 324/262 X |
| 4,454,473 | 6/1984 | Rosauer .............................. 324/262 |

FOREIGN PATENT DOCUMENTS

| 449234 | 4/1975 | U.S.S.R. .............................. 324/262 |
| 748231 | 7/1980 | U.S.S.R. .............................. 324/262 |

Primary Examiner—Gerard R. Strecker
Attorney, Agent, or Firm—Watson Cole

[57] ABSTRACT

A device for transmission of signals between two units which are movable relative to each other without having to use rotating slip rings or the like. The signal transmitting conductors are disposed close to a point on the center axis of a rotating holder for the signal source. This results in minimum fatigue of the conductors, which in turn permits a long life of the conductors. The signal source is journalled in the holder and can be prevented from rotating around its center axis. The device can also be used to transmit a medium such as a coolant between two units.

10 Claims, 3 Drawing Figures

DEVICE FOR USE IN EDDY CURRENT TESTING FOR TRANSMISSION OF SIGNALS BETWEEN A SIGNAL PROCESSING DEVICE AND A SIGNAL SOURCE

TECHNICAL FIELD

The present invention relates to a device for transmission of signals and/or media between a signal processing device (e.g. in the form of a measuring and control device) and at least one signal source associated with the processing device and being movable, for example rotatable, relative to an object to be tested. The device comprises a holder, preferably in the shape of a solid of revolution journalled to turn about a turn axis in a bearing in or on a base member; at least one transducer or other signal source eccentrically journalled in or on the holder; at least one mechanical connecting link, for example a tube, arranged between the base member and the signal source; a first coupling, via which the at least one mechanical connecting link is connected to the base member and the centre of which is located on or near the turn axis of the holder; a second coupling via which the at least one mechanical connecting link is connected to the signal source, and at least one signal conducting means between the processing device and the signal source and being disposed through or near the couplings.

PRIOR ART

A frequently occurring problem in connection with the transmission of signals and media between a movable transducer and a more stationary unit, for example a measuring device, is that it is not possible to transmit signals and media in a simple manner. Electric cables and medium hoses alone cannot be used, since these are easily destroyed by twisting because of the movement and rotation of the transducer relative to the measuring device. In eddy current testing, for example, attempts have been made in certain cases to overcome the problem by making use of slip ring transmissions for passing the electrical signals between the signal source and the signal processing unit. However, slip rings are very easily damaged, making them a weak link in the measuring system. In eddy current testing, rapid signal transmissions with high stability as regards transition resistance, etc., are often required, which means that a simple galvanic connection between the fixed and movable components is normally superior.

One object of the present invention is to provide a solution to the above-mentioned problems and other problems associated therewith.

SUMMARY OF THE INVENTION

The invention is characterized in that each of the first and second couplings consists of flexible couplings for the transmission of a rotary motion and/or a torsional moment, for example hollow flexible bearings which are motion restricted by turn-limiting means, so that the signal source is prevented from rotating to any major extent relative to the base member, thus preventing the signal conducting means or media hoses from being damaged by excessive twisting.

The invention can be employed in, for example, crack detection by means of eddy current testing and in this case the signal source will be a coil, the electrical impedance changes in which can be monitored to give information about, for example, surface cracks in a test object. Other signal sources can, of course, be used and the signal conducting means could be optical fibers.

One field of application of special interest for the invention however, is eddy current testing, as described, for example, in Swedish Patent Application No. 7507857-6, United Kingdom Patent Application No. 2041535 and U.S. patent application Ser. Nos. 621,916 (filed in the name Törnblom on June 15, 1984), now abandoned; 680,258 (filed in the name Törnblom on Nov. 13, 1984), now U.S. Pat. No. 4,646,013; 699,594 (filed in the name Törnblom on Feb. 8, 1985), now U.S. Pat. No. 4,661,777; and 702,314 (filed in the name Törnblom on Feb. 15, 1985), now U.S. Pat. No. 4,703,265. Thus, the invention can be regarded as an important complement to these separate inventions, which, can considerably increase the performance as far as the speed and accuracy of scanning is concerned.

The reason for a frequent need to rotate the coil of an eddy current tester is a desire to scan as large a portion of the surface of a test object as possible per unit of time. By superimposing a rotary motion on, for example, the normal travelling movement of the coil relative to the test object, this can be achieved in a simple manner. Another reason may be that it is desired, for example in connection with eddy current testing, to cross the cracks to be detected as close to perpendicular as possible.

BRIEF DESCRIPTION OF THE DRAWINGS

The invention will now be further described in greater detail, by way of example, with reference to the accompanying drawings, in which.

DESCRIPTION OF PREFERRED EMBODIMENT

Figure 1:
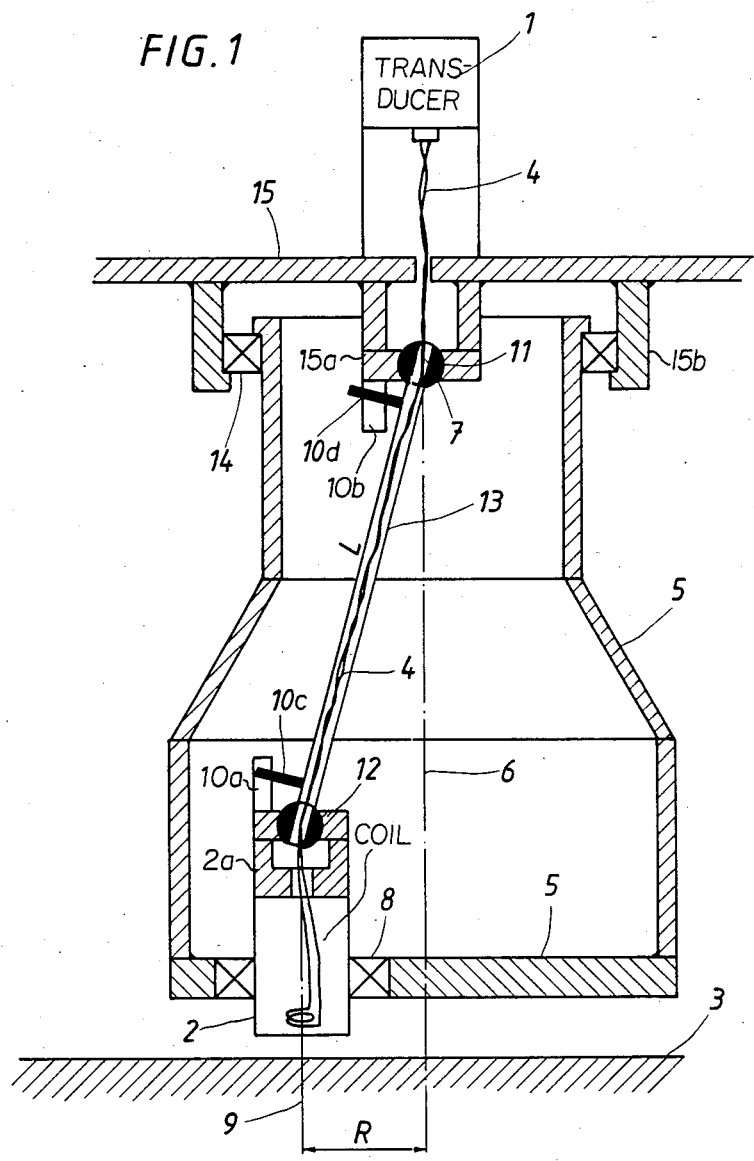
FIG. 1 is a cross-section through a device according to the invention.

For simplicity, the following description has been restricted, by way of example, to an application of the invention in which the signal source (or transducer) consists of a coil 2 of eddy current type with an associated electronic measuring unit 1 serving as the signal processing device.

The transducer 2 is able to move in a circular path about a center axis 6 of a holder 5 shaped as a solid of revolution. The transducer 2 is used to inductively sense the surface of a test object 3 and detect the presence therein of discontinuities such as, for example, surface cracks and the like. The transducer 2 contained within housing 2a which is journalled by means of a bearing 8 in the holder 5, which in turn is journalled in a base member 15 by means of a bearing 14 mounted at support member 15b. The holder 5 may be made to rotate in many ways, for example via a motor and chain (not shown) or a driven friction wheel or belt.

Because of the eccentric location of the transducer 2 in/on the holder 5, the transducer 2 will be moved around a circular path across the surface of the test object when the holder 5 rotates. Because the transducer 2 is journalled in the holder 5 via the bearing 8, the transducer 2 can be adapted so as not to rotate about its own center axis 9 while rotating with the rotation of holder 5, as is discussed more fully hereinafter.

The transducer 2 is connected to the base member 15 by means of a connecting link in the form of a tube or arm 13 having upper and lower flexible bearings 11 and 12, the link 13 thereby being able to swing within the holder as a "pendulum arm". Inside the pendulum arm 13 one or more flexible signal connecting means 4, for example electrical cables, are disposed. The connecting means 4 connect the transducer 2, for example galvanically, to the electronic measuring unit 1. The connecting means 4 may consist of both signal and media (e.g. liquid coolant) conductors. Thus the arm 13 may contain one or more electrical cables and one or more water hoses.

The pendulum arm 13 may be made to be extensible in the longitudinal direction so that the transducer coil 2 may, for example, be made to move three-dimensionally relative to the test object 3, which may be of value in the case of, for example, measurements over a curved surface of the test object.

The bearings 11 and 12 shown in FIG. 1 are universal joints and these are a convenient form of flexible coupling. The center axis 6 is suitably substantially normal to the surface of the test object 3. Flexible bearing 11 is mounted in support member 15a extending from non-rotating base member 15, and flexible bearing 12 is mounted in transducer housing 2a as shown in FIG. 1.

Projection 10a extends from transducer housing 2a and projection 10b extends from support member 15a as shown in FIG. 1. By providing the pendulum arm 13 with respective projections 10c and 10d adjacent to each end thereof, which abut against respective projections 10a and 10b, the transducer 2 is prevented from rotating through a full 360° relative to the measuring unit 1, so that the signal connecting means 4, and where provided, media conductors, are not damaged by twisting.

By placing the upper bearing 11 so that its fulcrum 7 is situated on the center axis 6 of the holder 5, a minimum movement at the fulcrum 7 will be obtained. Due to this, the mechanical fatigue on the signal connecting means and/or media conveyors will, for example, be small, provided they are disposed through or close to the fulcrums in the bearings 11 and 12. It should be noted that the upper fulcrum 7 is largely stationary relative to the measuring unit 1 in spite of the fact that the transducer 2 may be rotating at a considerable speed relative to the test object 3. It is similarly advantageous if the flexible bearing 12 adjacent to the transducer 2 is located at the axis of rotation 9 of the transducer 2.

Practical tests with flexible conductors 4 of standard type, for example electrical conductors of strips of metallic foil, have shown that it is possible to achieve very long operating times without any rupture occurring in the conductors. The use of foil cables has the additional advantage of being inexpensive and robust.

The holder 5 may advantageously rotate continuously during use of the device, but may also, if desired, periodically reverse its direction of turning to give a reciprocating motion. In this way the transducer 2 may, for example, be made to oscillate over the test object 3, which is valuable for certain applications, for example on surfaces which are difficult to reach or near an edge region of the test object. The holder 5 may have the shape of, for example, an arm.

By locating the center axis/axis of rotation 6 of the holder 5 perpendicular to the surface of the test object 3, the distance between the transducer 2 and the test object can be kept substantially constant, which, for example when sensing eddy currents, may be a considerable advantage. The same thing applies to the center axis 9 of the transducer 2. For keeping this so-called "lift-off" distance constant, it is advantageous to use an automatic system which, for example, raises and lowers the base member 15 while simultaneously adjusting the angle of the center axis 6 relative to the test object 3.

During testing of hot objects such as, for example, continuously cast billets, cooling of the transducer 2, is often required. Therefore, the medium may consist of cooling water which is conducted to and from the transducer 2 via hoses located in the arm 13. Also the bearing 8 may need cooling by water in a similar way, for example via cooling water channels fed to the bearing via the transducer 2.

The invention also comprises those special cases where one or more of the bearings have been replaced by flexible, for example resilient, mechanical arrangements. As an example of this, both the bearings 11 and 12 in FIG. 1 may be replaced by helical springs which are then to be regarded as bearings. Such a spring will then also include a carrying function. In other words, the spring may act simultaneously as a bearing and as a carrier for the signal source 2.

Since one of the basic thoughts behind this invention is to overcome the problems caused by fatigue in movable transducers, it is particularly important that the conductors do not break at the point of maximum stress which, for example, may be within the bearings 11 and 12, where although the movement is greatly limited it is nevertheless not negligible. In order further to reduce the risk of fatigue damage, it is therefore advantageous to place the signal conducting means in, for example, a polyurethane hose which is both flexible and fatigue-resistant, whereby the bending of the signal conducting means is distributed in a more uniform way along an extended length thereof. At the same time, the position of the signal conducting means, which is often soft, is stabilized. When used with eddy current measuring, for example, this may be a significant advantage from the point of view of the measurement technique used.

In certain applications involving considerable endurance stress, it may be advantageous, for the same reason, to use as the signal conducting a helical or folded wire or foil, in order thus to reduce the bending of the wire or foil per unit length. This, of course, increases the life of the conductor.

The term "signal conducting means" comprises a range of differing components such as, for example, a fiber optic link. In a similar way, the term "signal source" embraces a wide range of different transducers for monitoring properties of the test object 3. The signal source may thus include any associated electronic equipment for a transducer which may be located in the immediate proximity of the transducer.

By "signals" is meant, in addition to conventional signals, also the transmission of electrical current which may be needed for the electrical energisation of the signal source.

When the signal source 2 rotates around the center axis 6 of the holder 5 in a path having a radius R, referring to FIG. 1 it is seen that it may often be important that the length L of the pendulum arm 13 is large compared to the radius R of the path of rotation, in order to minimize the movement at the fulcrum 7. Practical tests have shown that the ratio L/R should be greater than 5 (preferably $>10$) to obtain a long life for the signal conducting means 4.

Figure 2:
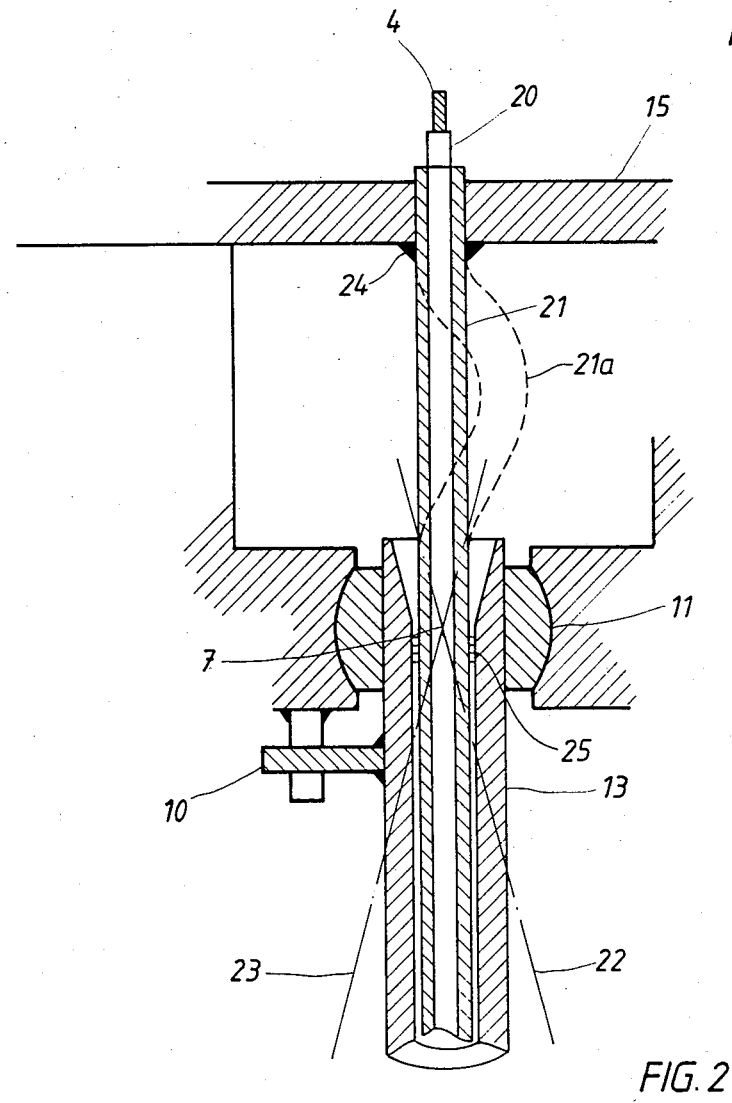
FIG. 2 shows, on an enlarged scale, one embodiment of a flexible bearing for use in the device of FIG. 1.

FIG. 2 shows, by way of example, in cross-section, one way in which the upper flexible bearing 11 may be constructed. It should be noted that the conductor 4 shown in FIG. 2 has a surrounding insulation 20 which is arranged in a polyurethane hose 21, which is fixed to the base at 24. When the pendulum tube 13 moves between its extreme positions 22 and 23, the hose 21 relieves the conductor 4 in an efficient way, which often considerably extends the life of the conductor. In order to prevent tension load in the conductor 4 and the hose 21, it is often desirable to arrange the hose 21 to form a loop or bend (as shown dotted at 21a) between the point 24 and the upper end of the tubular arm 13. Inside the pendulum tube 13, the hose 21 can be fixed to the tube (e.g. at 25) with, for example, silicone rubber or the like.

Figure 3:
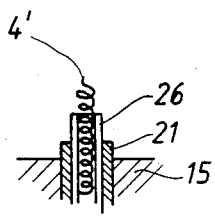
FIG. 3 is a detailed view of a modified arrangement of the connecting means to the transducer.

FIG. 3 shows a scrap section of the upper part of FIG. 2 showing a modified arrangement. In this modification a conductor 4' is formed as a helix passing through a flexible medium-conveying flexible tube 26.

The devices described with reference to the drawings can be varied in many ways within the scope of the following claims.

I claim:

1. A device for transmission of signals between a signal processing device and a signal source mounted in a housing being movable relative to a test object, comprising a non-rotating base member, a holder having an end face adapted to be positioned adjacent a surface of the test object for rotatably supporting the signal source, a support member extending from said non-rotating base member, and including a first bearing for rotatably supporting the holder about a rotation axis intersecting said test object, a second bearing in the end face of the holder by which the signal source housing is eccentrically journalled to the holder, a connecting link in the form of a tube interconnecting the non-rotating base member and the signal source housing, a first coupling mechanically connecting the connecting link to the non-rotating base member adjacent to the rotation axis of the holder, a second coupling mechanically connecting the connecting link to the signal source housing, and signal conducting means within the connecting link extending between the signal processing device and the signal source through the first and second couplings, said first and second couplings being flexible couplings permitting the connecting link to rotate relative to the non-rotating base member, and rotation limiting means for substantially preventing the signal source to rotate more than 360 degrees relative to the non-rotating base member and including projections extending outwardly from the tube and engaging respective projections extending from said signal source and said non-rotating base member adjacent to the first and second couplings, said connecting link tube being adapted to allow liquid coolant to be transported to the signal source.

2. A device according to claim 1, in which each of said first and second couplings comprises a universal joint.

3. A device according to claim 2, in which the connecting link is adapted to move in a lengthwise direction thereof through at least one of the universal joints.

4. A device according to claim 1, further comprising at least one electrical conductor cable surrounded by a flexible hose and located within the connecting tube and extending therefrom adjacent to at least one of the flexible couplings.

5. A device according to claim 1, in which the ratio between the length of the connecting link and the radius of rotation of the signal source housing is greater than 5.

6. A device according to claim 1, in which the signal conducting means is an electrical conductor and the connecting link tube surrounds the conductor.

7. A device according to claim 6, in which the electrical conductor has a bend between the first coupling and a point of attachment of the conductor to the non-rotating base member.

8. A device according to claim 1, in which the rotation axis of the holder is substantially normal to a surface of the test object confronting the holder and the signal source.

9. A device according to claim 1, in which the connecting link is adapted to be extensible in a longitudinal direction thereof.

10. A device according to claim 1, in which the signal source is an induction coil and the signal processing device is an eddy current crack detector.

* * * * *